United States Patent [19]

Spanswick

[11] Patent Number: 4,638,814
[45] Date of Patent: Jan. 27, 1987

[54] ELECTRON ACCELERATOR UNIT FOR ELECTRON BEAM THERAPY

[75] Inventor: Keith A. Spanswick, Oceanport, N.J.

[73] Assignee: Siemens Medical Laboratories, Walnut Creek, Calif.

[21] Appl. No.: 649,392

[22] Filed: Sep. 11, 1984

[51] Int. Cl.$^4$ .............................................. A61N 5/00
[52] U.S. Cl. ....................................................... 128/804
[58] Field of Search ................... 128/303 B, 362, 376, 128/419 R, 422, 783, 802, 804; 250/345, 366, 368, 398, 400, 453.1, 454.1, 493.1, 503.1; 378/64–65, 147–148

[56] References Cited

U.S. PATENT DOCUMENTS

| | | | |
|---|---|---|---|
| 3,861,807 | 1/1975 | Lescrenier | 378/65 |
| 4,123,660 | 10/1978 | Horwitz | 378/65 |
| 4,140,129 | 2/1979 | Heinz et al. | 128/783 |
| 4,256,966 | 3/1981 | Heinz | 378/65 |

OTHER PUBLICATIONS

Lillicrap et al., "British Journal of Radiology", vol. 47, Mar., 1974, pp. 193–195.
Fischer and Co, Inc, Catalog No. 14, May 1, 1924, p. 45.

Primary Examiner—William E. Kamm
Attorney, Agent, or Firm—Mark H. Jay

[57] ABSTRACT

An electron accelerator unit comprises a source of an electron beam and means for finally directing at least a portion of the beam to a therapy site. The directing means is mechanically independent of, and electrically isolated from, the source of the electron beam.

In the preferred embodiment, means are provided for aligning the source and the directing means using beams of light which are directed towards a target area on the directing means.

14 Claims, 3 Drawing Figures

SUPPORT PLATE 22 ACCURATELY POSITIONED

SUPPORT PLATE 22 ACCEPTABLY MISPOSITIONED

SUPPORT PLATE 22 AT POSITION OF MAXIMUM ACCEPTABLE MISPOSITIONING

SUPPORT PLATE 22 UNACCEPTABLY MISPOSITIONED

ELECTRON ACCELERATOR UNIT FOR ELECTRON BEAM THERAPY

BACKGROUND OF THE INVENTION

The invention relates to electron beam therapy and equipment used for it.

In electron beam therapy, a beam of electrons is directed to a treatment site. Typically, this is brought about using a relatively large electron accelerator unit. This apparatus includes a source of an electron beam, to which is mechanically attached an electron applicator. (The term "electron applicator", as used herein, includes cones and other compensating members and generally encompasses all devices which are placed on or in close proximity to a patient to finally direct the electron beam to the desired treatment site.)

It is now desired to carry out electron beam therapy in an intra-operative environment, i.e. inside the body of a patient through an incision in the patient's skin. This is unfeasable with conventional electron accelerator units.

One reason for this is that the electron accelerator unit is large and unwieldy. It is dangerous to move the electron applicator of such a unit within a relatively small operative incision without risking injury to the patient.

Another reason why intra-operative electron beam therapy is now unfeasable results from governmental and medical regulations which apply to the conduct of intra-operative procedures. These regulations provide that no patient may be subjected during an operation to ground leakage currents which exceed, e.g., five microamperes. This is because (1) blood and body fluids are good electrolytes and excessive current flow can injure a patient and (2) other apparatus (such as that used to monitor the patient's body functions) may be disturbed by excessive current flows. Since ground leakage currents exceeding five microamperes may flow between the patient and a conventional accelerator unit as a result of contact between the electron applicator and the patient's body, such conventional equipment is unsuitable for intra-operative therapy.

It would be advantageous to provide an electron accelerator unit which is suitable for intra-operative use.

One object of the invention is to provide an electron accelerator unit which can be used for electron beam therapy in an intra-operative environment.

Another object is to provide such a unit which is easily mechanically maneuverable with respect to the patient.

Yet another object is to provide such a unit in which there is no possibility of current flow between the unit and the patient.

A further object is to provide such a unit in which an operator cab view the treatment site directly, without using television equipment.

Still a further object is to provide a unit which is easy to use and cost-effective.

Still a further object is to generally improve over the prior art.

SUMMARY OF THE INVENTION

In accordance with the invention, the means which finally directs an electron beam to a therapy site is mechanically independent of the source of the beam and is also electrically isolated from it. Preferably, this directing means is separately and independently supported on its own support, whereby it can be fixed with respect to the patient at a location remote from the source of the electron beam.

Further advantageously, there is provided a means for aligning the source and the directing means, whereby the electron beam is easily and accurately directed into the directing means. In a preferred embodiment, this aligning means is adapted to a establish a predetermined distance between the source and the directing means. In this way, beam intensity at the desired treatment site can be accurately adjusted.

The invention will be better understood with reference to the following drawings and the detailed description of preferred embodiments.

BRIEF DESCRIPTION OF THE DRAWINGS

Exemplary and non-limiting preferred embodiments of the invention are shown in the drawings, in which.

DETAILED DESCRIPTION OF PREFERRED EMBODIMENTS

Figure 1:
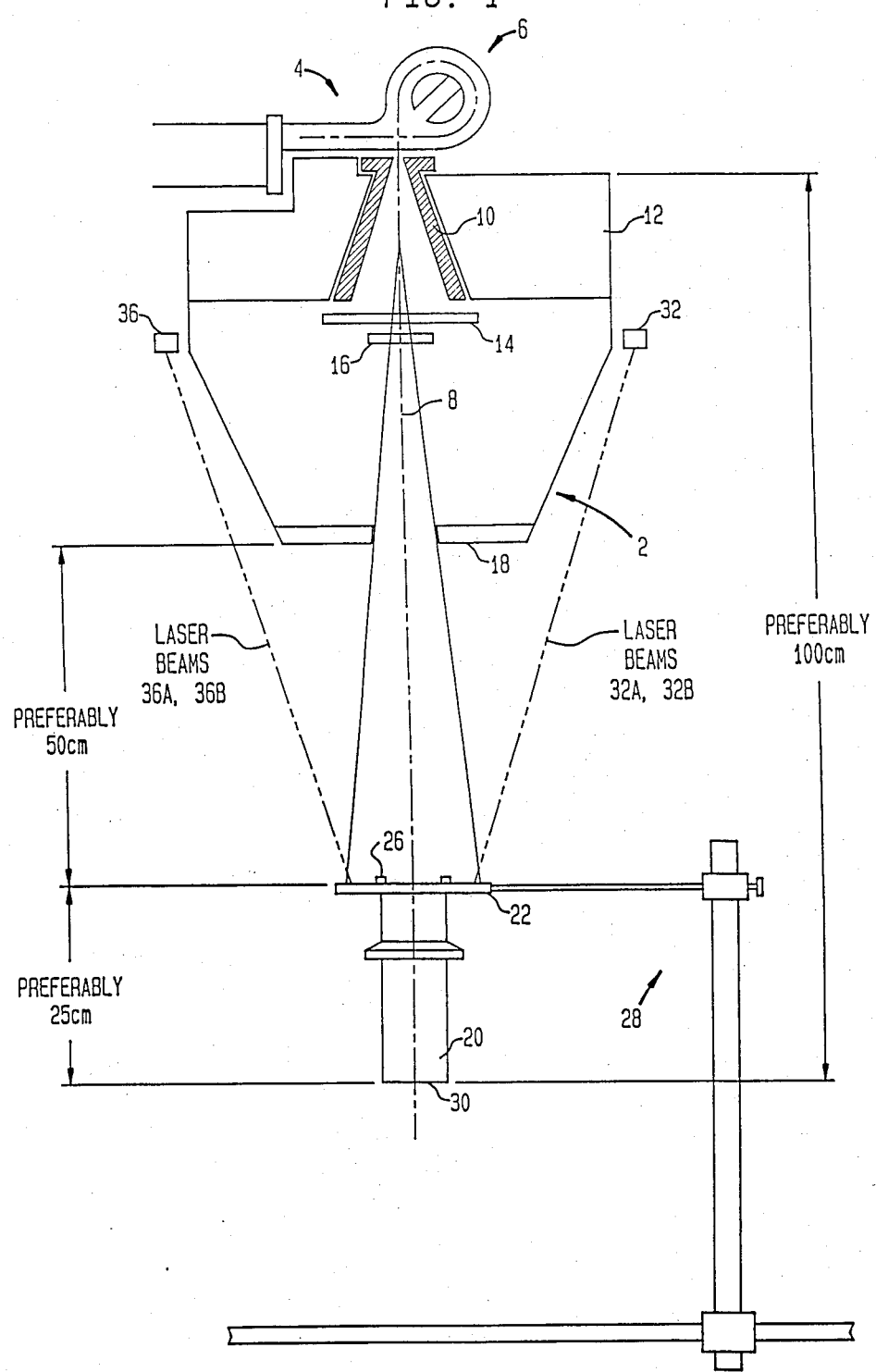
FIG. 1 is a schematic and partially cutaway view of a preferred embodiment.

A head generally indicated by reference numeral 2 of an electron accelerator unit supports a waveguide 4 through electrons are directed. The waveguide 4 has a bending chamber 6 which produces a pencil-shaped electron beam 8 in the throat of an electron absorber 10. The electron absorber 10 has a generally conical interior and is made of an appropriately electron-absorbing material. Shielding 12 surrounds the electron absorber 10 to protect users and the patient.

The electron beam 8 is then directed on a scattering system schematically indicated by reference numeral 14. The scattering system 14 may be of the two foil type and may be constructed as a removable foil slide. The scattering system 14 restricts the electron population of the beam 8 to electrons having less than some predetermined maximum energy.

The beam 8 is then directed to electron dose chambers which are generally indicated by reference numeral 16. These electron dose chambers 16 monitor the characteristics of the electron beam 8 to produce warning signals using suitable apparatus (not shown) if the electron beam 8 has any discrepant characteristics.

Thereafter, the beam 8 is passed through a primary collimator generally indicated by reference numeral 18. In this embodiment, the primary collector 18 is a plate with a circular opening, although the opening may be differently shaped to match other components described below if those components create a field which is noncircular.

The apparatus described above is known by itself, and is not part of the invention. The construction of the head 2 may be changed in any appropriate manner. For purposes of the invention, it is only important that the head 2 is a source of an aligned and somewhat collimated electron beam 8.

The beam 8 is directed towards an electron applicator generally indicated by reference numeral 20. As used herein, the term "electron applicator" includes any element (such as a cone) which is used to finally direct the electron beam to a particular treatment site (not shown) in or on a patient (not shown). To accomplish this, the electron applicator 20 is placed e.g. in an incision (not shown) in a patient's body (not shown) to treat a tumor at a treatment site (not shown).

Figure 2:
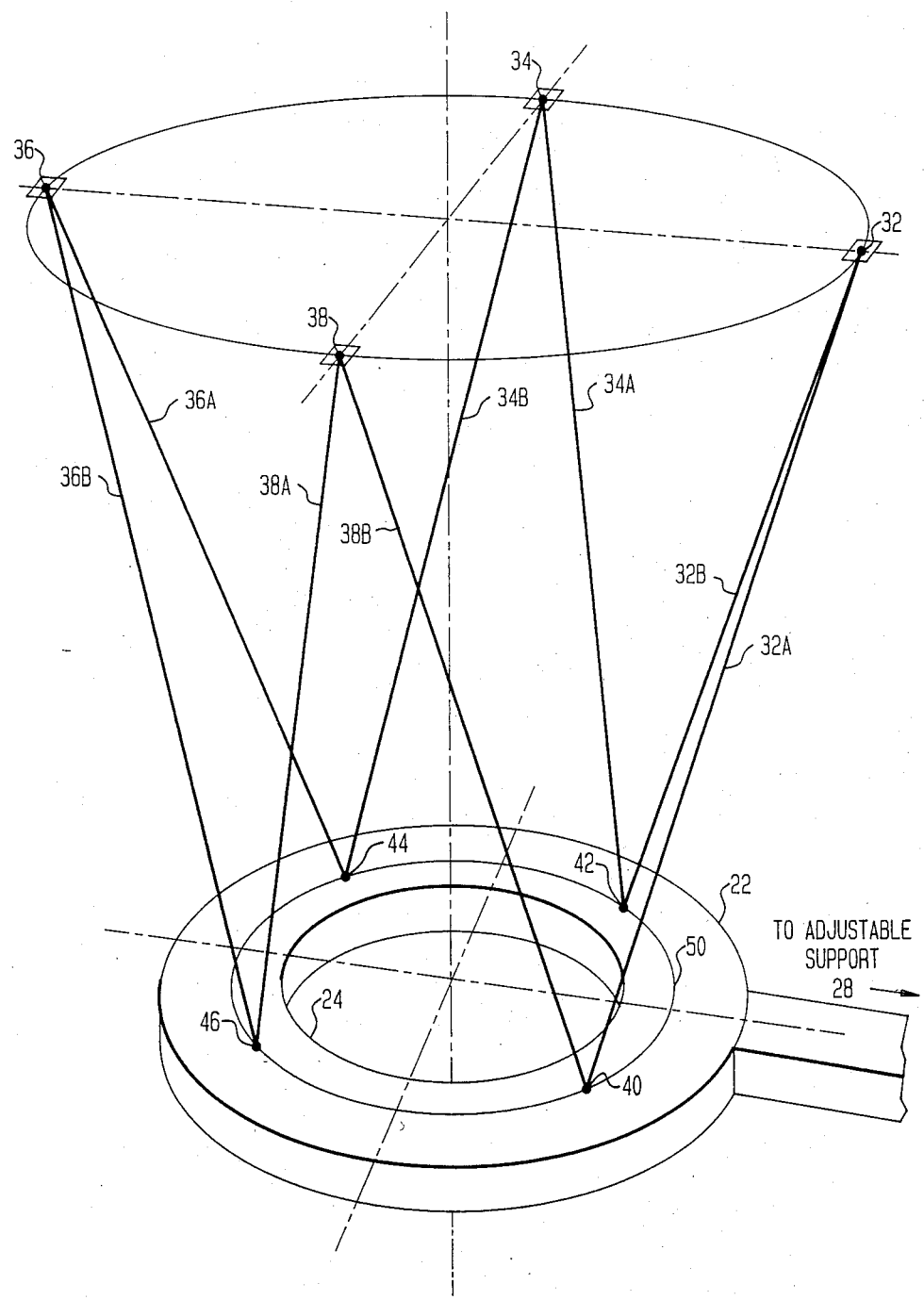
FIG. 2 is a schematic perspective drawing of a portion of the preferred embodiment.

To support the electron applicator, there is provided a support plate 22. The support 22 is annular and has a central circular hole 24 (FIG. 2). The support plate 22 is adapted to receive any one of a plurality of electron applicators 20, which can be dropped into the hole 24. Each of the electron applicators 20 has an annular flange 26 which rests upon the support plate 22 so that the electron applicator 20 does not fall through the hole 24. Means (not shown) are preferably provided to lock the electron applicator 20 to the support plate 22, but this is not part of the invention and one skilled in the art can construct such means or have it made. For the purpose of the invention, it is only important that the hole 24 and the electron applicators 20 be dimensioned with sufficiently close tolerances that the field defined by the electron applicator 20 has a predictable and stable location with respect to the support plate 22.

The support plate 22 is connected to and supported by an adjustable support generally indicated by reference numeral 28. The support 28 is of a type known by itself; it serves to mount the support plate 22 (and thus any electron applicator 20 mounted to it) so that proper positioning of the electron applicator 20 is achieved. Details of the support 28 are not shown; they are known to those skilled in the art. Preferably, the support 28 is mounted to the patient couch or operating table (not shown); this facilitates alignment as described below.

The electron applicator 20, support plate 22, and adjustable support 28 are all mechanically independent of, and electrically isolated from, the head 2. Thus, physical movement of the head 2 is not dangerous, and no current flows between the patient and the head 2.

It is necessary to accurately align and space the electron applicator 20 from the head 2 of the electron accelerator unit. Alignment is necessary so that the output end 30 of the electron applicator 20 is properly coincident with the beam 8, and spacing is necessary because the intensity of the beam 8 at the output end 30 (and thus at the treatment site) is a function of the distance between the open end 30 and the head 2.

To facilitate proper adjustment of the electron applicator 20 with respect to the head 2, there are provided four laser units 32, 34, 36, and 38. As will become apparent below, the laser units 32, 34, 36, and 38 project beams of light toward the support ring 22, and the beams are arranged in a predetermined mutual orientation. When the beams form a predetermined pattern on the support ring 22, the support ring 22 is properly located with respect to the head 2.

The laser units 32, 34, 36, and 38 are all spaced around the head 2 at 90° intervals; as shown in FIG. 1, the laser units 32, 24, 36, and 38 are mounted to the head 2 and project radially outwardly from it, so that each laser unit 32, 34, 36, and 38 has an unobstructed view of the support ring 22.

The laser units 32, 34, 36, and 38 are preferably the same; they are preferably helium-neon lasers with two fiber optic cables (not shown) terminated by focussing lenses (not shown). In this example, each laser unit uses a beam splitter to split the laser beam into two parts and each part is directed through a corresponding one of the fiber optic cables. It is not necessary that four laser units 32, 34, 36, and 38 be used; it would for example be possible to use one laser and a multiple beam splitter to split the laser beam into as many beams as are required. Four laser units 32, 34, 36, and 38 are used for manufacturing convenience.

FIG. 2 shows the light beams from the laser units, 32, 34, 36, and 38 in more detail. The light beams are identified with alphabetic suffixes, so that the two beams 32A and 32B are produced by laser unit 32, the two beams 34A and 34B are produced by laser unit 34, and so forth. The fiber optic cables in each of the laser units 32, . . . 38 are arranged such that adjacent pairs of beams of light intersect at predetermined points with respect to the head 2. In this example, beams 32A and 38B intersect at point 40, beams 32B and 34A intersect at point 42, beams 34B and 36A intersect at point 44, and beams 36B and 38A intersect at point 46. The four intersection points 40, 42, 44, and 46 are all equidistant from the head 2 and in this example, they are located at the corners of a square.

A circle 50 is scribed on the top surface of the suport plate 22. When a user sees four punctiform dots of light arranged in a square lying on the circle 50, this indicates that the support plate 22 is properly oriented with respect to the head 2. The preferred adjustment procedure to achieve this alignment begins when the electron applicator 20 is inserted into an operative incision in a patient (not shown) so that the output end 30 is directly over a treatment site at which a tumor (not shown) is to be treated. A physician or other user then verifies that the electron applicator 20 is properly oriented by looking into it and viewing the treatment site. After the proper orientation of the electron applicator 20 has been verified the support 28 is locked in position. The electron applicator 20 is thereby fixed with respect to the patient couch or operating table (not shown).

Figure 3A:
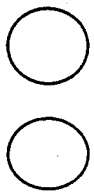
FIG. 3 schematically shows various patterns indicating alignment and disalignment in the preferred embodiment.
Figure 3B:
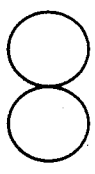
Figure 3C:
Figure 3D:
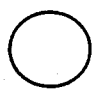

The operating table is then moved until four illuminated regions are visible on the top surface of the support ring 22. The operating table is then raised or lowered until at least one of the intersection points 40, 42, 44, or 46 is visible as a single point, and the operating table is then moved once again until that point is aligned with circle 50. If the other intersection points are not punctiform on the circle 50, the support plate 22 is not precisely perpendicular to the beam 8. This nonalignment is then corrected by appropriate movement of the operating table. For example, if a point on the top surface of the support ring 22 is either closer to or further away from the head 2 than the proper spacing, an intersection point at that location will either appear as an elongated body (FIG. 3B), two touching dots (FIG. 3C), or two separated dots (FIG. 3D), the separation of the dots in the last case increasing with increasing mispositioning of the support ring 22 relative to the head 2. It is preferred that the operating table be so oriented with respect to the beams of light 32A, . . . 38B that an operator can easily institute corrective motion of the operating table.

There need not be eight beams of light, nor four intersection points, and the intersection points may be arranged in a non-square pattern. This arrangement is preferred because it matches the drive system for the patient couch and is easy to use, but it is not required for the practice of the invention.

Advantageously, the head 2 is spaced such that the treatment site can be viewed directly through the electron applicator 20, even when the patient is underneath the head 2.

Lasers are used for laser units 32, 34, 36, and 38 because this produces exceedingly sharp beams of light 32A, ... 38B. Sharpness is a prerequisite because proper electron beam therapy requires precise positioning. In this example, each of the beams of light 32A, ... 38B is 2 mm in diameter. If two dots touch each other on the circle 50, this means that the maximum plan misalignment of the support ring 22 is 2 mm. This corresponds to the angular error of 3° which is acceptable. Thus, if two adjacent dots of light on the support plate 22 are separated from each other, then the support plate 22 is mispositioned at that location and more adjustment is required. Mispositioning of the support plate 22 is therefore easy to detect.

The top of the electron applicator 20 may advantageously function as a secondary collimator; the dimensions of the support ring 22 and flange 26 in this example are chosen so that the beam 8 is collimated more narrowly than it is when it emerges from the primary collimator 18. For example, the primary collimator 18 may be chosen to produce a 20 cm diameter beam at the treatment site and the secondary collimator may be chosen to produce an 18 cm diameter beam at the same location. Thus, the secondary collimator collimates the beam more narrowly than does the primary collimator.

Those skilled in the art will understand that changes can be made in the preferred embodiments here described, and that these embodiments can be used for other purposes. Such changes and uses are within the scope of the invention, which is limited only by the claims which follow.

What is claimed is:

1. An electron accelerator unit for electron beam therapy, comprising:
   a source of an electron beam;
   means for finally directing at least a portion of said beam to a therapy site, said directing means being mechanically independant of, and electrically isolated from, said source, and having a target area; and
   means for aligning said source with said directing means, said aligning means comprising means for projecting at least one beam of light from the source toward said target area.

2. The unit of claim 1, wherein the target area is planar and a circle is scribed on it.

3. The unit of claim 1, wherein said projecting means projects a plurality of beams upon the target area in a manner that when said directing means and said source are aligned, the beams are arranged in a predetermined geometrical relationship on the target area.

4. The unit of claim 1, wherein said aligning means comprises means for establishing a predetermined distance between said source and said directing means.

5. The unit of claim 1, wherein said establishing means comprises means for projecting at least two intersecting beams of light from the source towards said directing means, the beams intersecting at said predetermined distance from said source.

6. The unit of claim 1, wherein said projecting means includes a laser.

7. An electron accelerator unit for electron beam therapy, comprising:
   a source of an electron beam;
   a primary collimator connected to said source to collimate the electron beam;
   means for directing the beam to a therapy site, said directing means being mechanically and electrically unconnected to said source;
   means for supporting said directing means; and
   means for indicating a position in which the directing means is properly aligned with and spaced from the source, said indicating means comprising means for projecting a plurality of pair of beams toward a plurality of predetermined intersection points, and a target area located on said directing means.

8. The unit of claim 7, wherein the primary collimator comprises a plate with a circular opening.

9. The unit of claim 7, wherein said directing means includes secondary collimator means for collimating the beam more tightly than the primary collimator.

10. The unit of claim 7, wherein the intersection points are the vertices of a regular polygon.

11. The unit of claim 10, wherein the polygon is a square.

12. The unit of claim 7, wherein said directing means includes means for receiving a plurality of interchangable electron applicators.

13. The unit of claim 7, wherein said indicating means comprises a light source and means for projecting a plurality of beams of light which intersect at a plurality of intersection points, the intersection points being equidistant from the source.

14. The unit of claim 13, wherein said projecting means comprises a plurality of fiber optic waveguides which are mounted to said source.

* * * * *